(12) United States Patent
Savaides et al.

(10) Patent No.: US 7,955,593 B2
(45) Date of Patent: Jun. 7, 2011

(54) METHOD AND COMPOSITION FOR REDUCING MALODOR IN PERMANENTLY WAVED HAIR

(75) Inventors: Andrew Savaides, Norwalk, CT (US); Rushi Tasker, Trumbull, CT (US); Jason Hier, Mount Kisco, NY (US); David Raymond, Hillsborough, NJ (US); Jennifer L. Russell, West Milford, NJ (US)

(73) Assignee: Zotos International, Inc., Darien, CT (US)

( * ) Notice: Subject to any disclaimer, the term of this patent is extended or adjusted under 35 U.S.C. 154(b) by 1319 days.

(21) Appl. No.: 11/352,543

(22) Filed: Feb. 13, 2006

(65) Prior Publication Data

US 2007/0190007 A1 Aug. 16, 2007

(51) Int. Cl.
*A45D 7/04* (2006.01)
(52) U.S. Cl. ........................ 424/70.2; 132/202; 132/204
(58) Field of Classification Search .................. 132/202, 132/204; 424/70.2
See application file for complete search history.

(56) References Cited

U.S. PATENT DOCUMENTS

| | | | |
|---|---|---|---|
| 4,560,554 A | 12/1985 | Kubo et al. | |
| 4,675,181 A | 6/1987 | Kamiishi et al. | |
| 4,834,971 A | 5/1989 | Klenk et al. | |
| 5,051,252 A | 9/1991 | Schultz et al. | |
| 5,352,443 A | 10/1994 | Kubo et al. | |
| 5,419,895 A | 5/1995 | Kubo et al. | |
| 5,441,729 A | 8/1995 | Salce et al. | |
| 5,554,363 A | 9/1996 | Nandagiri et al. | |
| 5,637,297 A | 6/1997 | Savaides et al. | |
| 5,851,516 A | 12/1998 | Borish et al. | |
| 5,972,322 A * | 10/1999 | Rath et al. | 424/70.11 |
| 5,988,180 A * | 11/1999 | Bergstrom | 132/204 |
| 6,254,646 B1 * | 7/2001 | Di La Mettrie et al. | 8/406 |
| 6,378,530 B1 | 4/2002 | Rezvani et al. | |
| 6,743,768 B2 * | 6/2004 | Gautschi et al. | 512/1 |
| 7,176,177 B2 * | 2/2007 | Lambrecht et al. | 512/27 |
| 2005/0042191 A1 * | 2/2005 | Travkina et al. | 424/70.7 |
| 2005/0096252 A1 * | 5/2005 | Dubois et al. | 512/1 |
| 2006/0207037 A1 * | 9/2006 | Fadel et al. | 8/406 |

OTHER PUBLICATIONS

Alpha-cedrene epoxide (alpha-cedrene epoxide, [online], Retrieved [Feb. 25, 2010], Retrieved from URL:< http://www.thegoodscentscompany.com/data/rw1001171.html>.*

\* cited by examiner

*Primary Examiner* — Frederick Krass
*Assistant Examiner* — Nannette Holloman

(57) ABSTRACT

A method and composition treatment is used to reduce post permanent odor in permed or waved hair. The malodor in permed hair is reduced by applying a leave-in aqueous treatment of pH 2.5-4.5 containing, hydrolyzed vegetable protein, polyquaternium-7, dimethicone and fragrance containing at least four components with water/octanol partition coefficient Log $K_{ow}$ or log P of 3-4.5. The post permanent odor in hair is reduced by (1) minimizing any reactions of hair with residual chemical compounds in hair after the perming process or after the oxidation step and (2) lessen or suppress any odoriferous compounds by decreasing their vapor pressure and (3) depositing in hair long lasting fragrance components to mask or change the malodor to be more pleasant.

14 Claims, No Drawings

METHOD AND COMPOSITION FOR REDUCING MALODOR IN PERMANENTLY WAVED HAIR

TECHNICAL FIELD

This invention relates to the art of permanently waving hair, and more particularly, to treatments for reducing malodor in the hair after the permanent waving operation.

BACKGROUND

The present invention relates to treatments for reducing the post perm odor in hair after the permanent wave operation. Post perm odors have been found to exist due to the use of hair reducing agents such Thioglycolic Acid, Thiolactic Acid, GTG, Cysteine, Cysteamine, Bisulfite or other product compounds that are entrapped into the porous structure of hair. The higher the porosity of hair the higher the binding affinity of the chemical compounds with hair or the higher the level of the odoriferous residues. Other factors that affect the binding affinity are molecular size, net change of reducing agent, electro-static charge of hair and the pH of the waving lotion.

Impurities, volatile mercaptans and other by-products that are formed from complex reactions of the reducing or oxidizing agents with hair are also responsible for the post permanent malodor.

The profile, duration and intensity of the post-perm odor appears to be dependent on the concentration, reducing agent type used and pH of the waving lotion. Another factor in the post-perm odor is the odor intensity of the reducing agent. Waving lotions prepared with Cysteine and Bisulfite are less odoriferous than Ammonium Thioglycolate (ATG) and Glyceryl Thioglycolate (GTG)

There are no specific reaction mechanisms for the formation of the odoriferous residues in hair from the different type of reducing agents. However the post-perm odor in hair from the different reducing agents or perm products is easily differentiated by the human nose.

The present invention involves the reduction of post-permanent wave odors of hair permed with the Cysteamine reducing agent. Cysteamine is a beta-mercapto ethylamine compound having the chemical structure:

$$HN_2—CH_2—CH_2—SH$$

The $pK_{SH}$ is 8.27, and 77.15 molecular weight with a net positive charge.

Due to the molecular size and positive charge, Cysteamine has a high binding affinity to hair. This implies that diffusion rates of Cysteamine into and out of the hair are very different.

The post-permanent odor in hair permed with Cysteamine is very different than other reducing agents, including Ammonium Thioglycolate (ATG), Glyceryl Thioglycolate (GTG), Cysteine and Bisulfite. This post-perm malodor in hair is referred or described by individuals as "corn chips", "burned pop corn" or "wet dog" or "cat urine". The intensity of the post-perm malodor is also amplified by cigarette smokers and the body chemistry of individuals.

The malodor is not affected by shampooing and it persists in hair for many weeks. The malodor is not noticeable in dry hair but appears to be strong and is released upon water contact. The malodor is continuously being released upon rewetting of the hair. This water adsorption and desorption behavior of odoriferous cysteamine by-products suggest that they exhibit a high vapor pressure point in water and that they are trapped in the hair shaft or are an integral part of hair as residues of modified keratin.

These odoriferous compounds claimed in U.S. Pat. No. 5,554,363 are due to the formation of Thiazolidines, which are reaction products between cysteamine and aldehydic or carbonyl functional groups in hair as shown below.

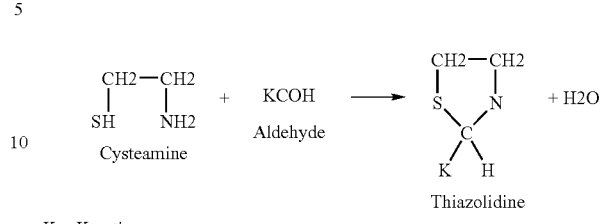

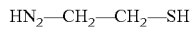
K = Keratin

The reaction between cysteamine and aldehyde or carbonyl functional groups occurs readily at pH 7.0-8.0, yielding stable five member ring Thiazolidine products. However, this reaction is very slow at pH less than 7.0 and very minimum at pH less than 4.0. The disclosure claims a pretreatment that reduces the post-perm hair odor by minimizing reactions of cysteamine with hair aldehyde sites or formation of the Thiazolidines with hair during the processing step. The pre-treatment includes carbonyl or aldehyde functional groups that will react with cysteamine producing non-odoriferous or pleasant smelling compounds in hair. However the effect of this pretreatment on hair mal-odor is very minimum and unsatisfactory.

Therefore, it is a principal object of the present invention to provide a hair treatment composition for reducing the odor in hair after a permanent wave operation which is long lasting and is easily applied to the hair after the permanent wave operation.

Another object of the present invention is to provide a hair treatment composition having the characteristic features described above which is retained in the hair fibers and avoids removal or dilution by normal hair shampooing or washing.

Another object of the present invention is to provide a hair treatment composition having the characteristic features described above which possesses a unique combination of fragrances that are retained by the hair fibers and effectively render any malodor to be more pleasant.

Another object of the present invention is to provide a hair treatment composition having the characteristic features described above which is capable of reducing, masking, and/or eliminating permanent wave malodor which occurs due to the re-wetting of hair fibers after a permanent wave operation.

Another object of the present invention is to provide a hair treatment composition having the characteristic features described above which also enhances the hair fibers by improving hair strength, shine, luster, and manageability.

Other and more specific objects will in part be obvious and will in part appear hereinafter.

DETAILED DISCLOSURE

The present invention is based on the identification of a chemical compound that has very similar odor characteristics to that of post perm odor of cysteamine permed hair. The chemical compound identified by the olfactory or nose sensory method is a natural occurring heterocyclic nitrogen compound called Tetrahydroquinoxaline (THQXLN) or cyclohexapyrazine. It has a molecular weight of 134.18 ($C_8H_{10}N_2$), boiling point of 73° C., flash point 198° F. and a vapor pressure of 0.1 mm Hg @ 20° C. The chemical structure of THQXLN is given below:

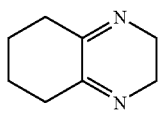

This compound is used in the flavor and food industry in breakfast cereals, condiment relish, gelatin pudding, gravies, milk products, non-alcoholic beverages, soft candy and soups.

The natural occurrence of Tetrahydroquinoxaline is found in Basmati Rice extract. The THQXLN in basmati rice assayed as 0.09 pp1000 and is not the major component. However it is the major odoriferous compound in the basmati rice due to its high vapor pressure point and good water solubility. At this low concentration, the dominant odor of THQXLN in the extract was first discovered and associated to that of cysteamine post-permed odor in hair. This was confirmed by spraying aqueous solutions of 0.0001% THQXLN on virgin unpermed hair tresses and compared them to Cysteamine permed tresses. Blind odor panel studies have shown that the malodor of hair tresses could not be differentiated, suggesting that the malodor of cysteamine permed hair is very close to that of THQXLN.

Further investigation has been carried out by GC/Mass Spectroscopy/Headspace analysis to identify the odoriferous compounds in hair. The method used to analyze the hair samples is referred to as Solid Phase Micro Extraction (SPME).

In SPME, after the volatile analytes reach a dynamic equilibrium in the headspace above the sample, they are adsorbed onto a stationary phase coated on a fused silica fiber and then they are thermally desorbed or injected onto a chromatographic column for separating. Because no solvent is injected onto the column, the separation efficiency and detection limits for the analytes are highly improved.

The GC mass spectroscopy using the SPME technique shows major molecular mass ion fragments at 36.00, 40.25 and 45.57 which are characteristic of heterocyclic nitrogen compounds. The abundance is the highest for the fragment mass ion of 36 identified as the THQXLN compound. The mass ion fragments of 40.25 and 45.57 are assigned or interpreted as Furaltadone and Morpholine compounds. The effect of water rinsing of tresses shows that both furaltadone and morpholine are affected by water rinsing and can be decreased up to 65-70% with 15 minutes of water rinsing. However THQXLN is not affected. This observation is in agreement that prolong water rinsing can help the post perm malodor but cannot eliminate it.

Thus residues are still left in hair and are not washed out with water or shampooing over a period of time. The approach in this invention is to minimize the post-perm malodor by (1) preventing or minimizing any reactions in hair after the permanent wave operation; (2) changing the physical properties of any residues in hair by increasing their water solubility, decreasing their vapor pressure point and their odor characteristics; (3) blocking the olfactory nose receptor sites where fragrance notes will reach these receptor sites much faster than the malodor notes; (4) strongly binding to hair a fragrance that will have a long lasting release for masking malodor on hair upon re-wetting.

In accordance with the present invention, a post treatment composition and method of application has been achieved which substantially reduces and/or eliminates the malodor found in permed or waved hair. In the present invention, the hair is permed according to the given directions. The post-perm, leave-in hair treatment is applied onto hair after the neutralizer is rinsed out from the hair and the rods are removed. This post-perm treatment is allowed to stay on hair for 10-15 minutes or more preferably for at least 24 to 48 hours before being shampooed and conditioned. The post-treatment composition is given below.

By referring to Table 1, the preferred formulation of the post-treatment composition of the present invention is fully detailed. In this presentation, each of the functional components forming the preferred composition is detailed with the quantity of each compound being provided both in the preferred range, as well as in the preferred, specific quantity. As detailed, the percentages are all provided as percent by weight, based upon the weight of the entire composition.

TABLE 1

Post Treatment Composition

| Ingredient | Amount (% w/w) Range | Preferred |
|---|---|---|
| Chelating Agent | 0.01-0.3 | 0.1 |
| Antistatic Agent | 0.25-1.0 | 0.5 |
| Fixative Agent | 0.1-2 | 1.5 |
| Conditioning Agent | 0.5-3 | 1.5 |
| Hair Strengthening Complex | 0.1-5.0 | 1.0 |
| Preservative | 0.05-0.6 | 0.1 |
| Solubilizer | 0.1-0.3 | 0.2 |
| Fragrance | 0.1-0.3 | 0.2 |
| pH Adjuster | q.s. to pH 2.5-4.0 | q.s. to pH 3 |
| Deionized Water | q.s to 100 | q.s. to 100 |

The principal functional ingredients incorporated into the preferred composition of the present invention comprises a combination of ingredients which interact with each other to achieve a unique formulation which attains the desired result. In particular, as shown in Table 1, a chelating agent ranging from between about 0.01% and 0.30% by weight based upon the weight of the entire composition is employed, with a 0.1% being preferred. In addition, between about 0.25% and 1.0% by weight based upon the weight of the entire composition of an antistatic agent is also incorporated into this preferred composition, with a 0.5% being preferred. Furthermore, between about 0.1% and 2.0% by weight based upon the weight of the entire composition of a hair fixative is incorporated into the preferred composition, with 1.5% being preferred. An additional ingredient incorporated into the preferred post-treatment composition of the present invention comprises between about 0.5% and 3.0% by weight based upon the weight of the entire composition of a conditioning agent, with 1.5% being preferred. Between about 0.1% and 5% by weight based upon the weight of the entire composition of a hair strengthening complex is incorporated into this composition, with 1.5% being preferred.

Another principal ingredient incorporated into the formulation of this invention is a blend of fragrances which enhance the overall beneficial effects of the post treatment composition. Preferably, the fragrance additives comprise between about 0.1% and 0.3% by weight, based upon the weight of the entire composition, with 0.2% being preferred. In addition, as is more fully detailed below, the fragrance blend comprises at least two components having an octanol/water partition coefficient Log $K_{ow}$ or log P greater than 4 and at least two components having a log P ranging between about 1 and 3.

By referring to Table 2, the preferred principal compounds employed in the post-treatment composition of the present invention are fully detailed, with each principal compound being defined for each of the functional ingredients. In this way, a full and complete disclosure of the post-treatment composition formulated in accordance with the present invention is readily apparent.

TABLE 2

Post Treatment Composition

| Ingredient | % w/w | Preferred % w/w | Function |
|---|---|---|---|
| Pentasodium Pentetate | 0.01-0.30 | 0.1 | Chelating Agent |
| Acetamidopropyl Trimmonium Chloride | 0.25-1.00 | 0.5 | Antistatic Agent |
| Polyquaternium-7 | 0.1-2.00 | 1.5 | Hair fixative |
| Solubilizer | 0.1-0.30 | 0.2 | |
| Fragrance | 0.1-0.3 | 0.2 | |
| Dimethicone and Tallow Trimmonium chloride | 0.5-2.5 | 1.5 | Conditioning Agent |
| Preservative | 0.05-0.600 | 0.1 | |
| Hydrolyzed Vegetable Protein PG- Propyl Silanetriol | 0.1-5.00 | 1.0 | Hair strengthening complex |
| pH adjustor QS to pH | 2.5-4.5 | | |
| Deionized Water | q.s. to 100 | q.s. to 100 | |

As is evident from the foregoing disclosure, the preferred hair strengthening complex comprises a copolymer of hydrolyzed vegetable protein and silicone. Preferably, the average molecular weight of this compound comprises 1800 daltons and is employed to strengthen the hair shaft and cortex. In this regard, low molecular weight proteins penetrate deep into the cortex and replenish longitudinal tensile properties of the hair, while the high molecular weight protein forms a film on the hair shaft for lubricating and reinforcing the cuticle cells, thereby increasing hair torsional strength.

In addition, in the preferred formulation, the pH of the composition is adjusted with phosphoric, citric, or ascorbic acid to range of between about 2.5 and 4, with the preferred pH comprising 3.0. It has been found that at this pH, the reaction between hair sites and the residual cysteamine, or other residues in the hair, are minimal. Also, any nitrogen volatile compounds are fully protonated and are more water soluble, thereby decreasing their vapor pressure.

In the preferred formulation, the composition must have a fragrance level of 0.1-0.3% or preferably at 0.2%. The fragrance composition is very unique and includes components for blocking the nose receptor sites as well as being substantive to hair for resisting water rinsing. More specifically, fragrance components must be retained in hair for several days after the permanent wave operation in order to mask any malodors upon re-wetting.

Selection of these fragrance components was based on the Octanol/water partition coefficient claimed in U.S. Pat. No. 5,540,853. This value is referred to as Kow or log P and is the ratio of the fragrance component concentration in the octanol phase to that of water. It is a measurement of the fragrance component's polarity. The higher the Kow value the lower the polarity or the more oil soluble the component.

Direct measurements of P are difficult and time consuming. Therefore indirect methods are used to calculate P values based on the chemical component structure and are referred to as Clog P. Input software such as SMILES (Kosmetikos "Smells Great! What's The Clog P?" March 1999, Global Cosmetic Industry) for Simplified Molecular Input Line System is used to calculate Clog P values.

The typical P values for organic chemicals can range from $10^{-3}$ to $10^7$. The fragrance components log P values range from −1 to 6. Fragrance components with low P values are hydrophilic and less substantive to hair and high P values are hydrophobic and highly substantive to hair. The fragrance components with high P values will resist water rinsing and provide the long lasting release of fragrance notes for masking the post perm malodor.

The major masking fragrance composition ingredients of the present invention are given below in Table 3 along with their Clog P values and molecular weight. Dipropylene Glycol and Benzyl Benzoate solvents are used in the fragrance composition of the present invention. The fragrance composition of the present invention preferably contains 4-Methyl-4-(methylthio)-2-pentanone and 2-Isobutyl-3-methoxypyrazine at less than 0.01%. These two ingredients are strong and have low Clog P values. These two key ingredients are very green in odor (grass, leaves etc.,) and will give the initial malodor coverage after the perm operation. These two ingredients have blended the offensive THQXLN odor on hair and blended to produce an overall green leafy odor profile. The other key ingredients have Clog P values that are higher than 4 and are the substantive notes that give long lasting masking effects of post-perm odor on hair. The fragrance notes were further blended with fruity and citrus notes yielding a pleasant odor through the two methods, blocking and blending.

TABLE 3

FRAGRANCE COMPOSITION

| Major Masking Ingredient | Clog P | MW |
|---|---|---|
| 1-(1,2,3,4,5,6,7,8-Octahydro-2,3,88-tetramethyl-2-naphthalenyl)ethanone (Iso E super) | 5.23 | 234.38 |
| Hexamethylindanopyran (Galoxolide) | 6.26 | 258.41 |
| Oxacyclohexadecene-2-one (Habanolide) | 4.65 | 240.00 |
| Ethylene Brassylate (Astratone) | 4.71 | 270.32 |
| Oxacycloheptadec-10-ene-2-one (Ambrettolide) | 5.37 | 252.98 |
| Dodecahydro-3,8,8, 11a-tetramethyl 5H-3,5a-epoxynaphth[2,1-c] oxepin (Ketamber) | 5.47 | 278.36 |
| 7-Methanoazuleno [5,6-b]oxirene 2h-2a (Andrane) | 4.69 | 220.36 |
| 3,3-dimethyl-5-92,2,3-trimethyl-3-cyclopenten-1-yl)-4-Penten-2-ol (Polysantol) | 4.35 | 222.37 |
| .2,2,6-trimethyl-a-propyl-cyclohexanepropanol (Timberol) | 5.80 | 226.40 |
| 4-Methyl-4-(methylthio)-2-pentanone | 1.21 | 146.25 |
| 2-Isobutyl-3-methoxypyrazine | 2.86 | 166.22 |

By incorporating the blend of the fragrances defined above in Table 3 into the post treatment composition as detailed in Tables 1 and 2, a uniquely constructed post treatment formulation is realized which is capable of achieving the desired reduction and/or limitation of malodor associated with permanently waved hair. In addition, by employing the composition of the present invention using the method steps described herein, a highly effective result is achieved which substantially satisfies the malodor problem, while also improving the strength, luster, shine, and manageability of the hair.

The invention accordingly comprises a composition possessing the features, properties, and relation of components, as exemplified herein, and the several steps and the relation of one or more of such steps with respect to each, as detailed herein, with the scope of the invention being indicated in the claims.

BEST MODE FOR CARRYING OUT THE INVENTION

In order to substantiate the efficacy of the creation of an effective malodor treatment system consisting of a post permanent composition and method of application, the following examples are presented. In the following disclosure, the universal applicability of this invention is fully detailed, along with the ability of the post-permanent composition of the present invention to substantially reduce and/or eliminate malodor associated with permanently waved hair while also providing long lasting physical enhancements to the hair fibers, including improved strength, luster, shine, and manageability. It is to be understood, however, that these examples are intended as a teaching of the best mode for carrying out the present invention and are not intended to limit, in any manner, the breadth of this discovery.

Example 1

The post-perm malodor was evaluated on a half head model with colored treated hair. One side of the model was treated with the pretreatment of Table 2 containing benzaldehyde and fragrance containing aldehyde and ketone components.

TABLE 4

Pre-Treatment Composition

| Ingredient | % w/w |
| --- | --- |
| Peg-40 Hydrogenated Castor Oil | 1.35 |
| PPG-26-Buteth-26 | 1.35 |
| Methyl Hydrocynnamic Aldehyde | 0.70 |
| Benzaldehyde | 0.25 |
| Glycerine | 0.20 |
| PEG-2 Oleammonium Chloride | 0.20 |
| Citric Acid | 0.14 |
| Propylene Glycol | 0.10 |
| Sodium PCA | 0.10 |
| Disodium EDTA | 0.10 |
| Simethicone | 0.10 |
| Water QS | 100 |

The hair was rolled onto appropriate rods and Waving Lotion #2 (color treated) composition of Table 5 was applied onto hair and processed for 20 minutes, the hair was rinsed for 10 minutes, followed with towel blotting.

TABLE 5

Waving Lotion Compositions % by w/w

| Ingredient | Lotion 1 N/R | Lotion 2 Color Treated |
| --- | --- | --- |
| Cysteamine HCl | 12 | 8.50 |
| Polaxamer 188 | 2 | 2 |
| Isoceteth-20 | 1.91 | 1.91 |
| MEA-Sulfite | 1.40 | 1.05 |
| Tetrasodium Etidronate | 1.20 | 1.20 |
| Ammonia | 1.08 | 0.80 |
| Fragrance | 0.64 | 0.64 |
| Glycine | 0.50 | 0.50 |
| Deonized Water QS to | 100 | 100 |

The hair was then neutralized for seven minutes with Neutralizer1 and Neutralizer 2 of Table 6 containing the fragrance composition of the present invention as detailed in Table 3.

TABLE 6

Neutralizer Compositions % by w/w

| Ingredient | Neutralizer 1 | Neutralizer 2 |
| --- | --- | --- |
| Hydrogen Peroxide | 2.15 | 2.25 |
| Dimethicone | 0.0035 | 1.20 |
| Laureth-23 | — | 1.10 |
| Adipic Acid | — | 0.50 |
| Dicetyldimonium Chloride | 0.70 | — |
| Alcohol Denat. | — | 0.19 |
| Tallowtrimonium Chloride | — | 0.20 |
| C11-15 Pareth 9 | — | 0.20 |
| Fragrance | 0.70 | 0.10** |
| Phosphoric Acid | 0.0069 | 0.070 |
| Pentasodium Pentetate | | 0.050 |
| Silica | 0.0069 | |
| Ext. Violet 2 | | 0.0003 |

**= fragrance composition Table 3

The hair was then rinsed and towel blotted. After the rods were removed from hair, the post treatment composition of the present invention defined in Table 7 was applied onto one side of the head.

TABLE 7

Post-Treatment Composition

| Ingredient | % w/w |
| --- | --- |
| Hydrolyzed Vegetable Protein PC- Propyl Silanetriol | 0.50 |
| Dimethicone | 0.45 |
| Acetamidopropyl Trimmonium Chloride | 0.37 |
| Fragrance Table 3 | 0.20 |
| Polyquaternium-7 | 0.13 |
| Laureth-23 | 0.11 |
| C11-15 Pareth-9 | 0.075 |
| Tallow Trimmonium chloride | 0.075 |
| Pentasodium Pentetate | 0.05 |
| Methylchloroisothiazolinone | 0.006 |
| Methylisothiazolinone | 0.001 |
| Citric acid QS to pH 3.15 | |
| Deionized Water QS to | 100 |

A malodor panel was carried out on the wet and dry model's hair. The malodor panel on wet hair shows below that 7 panelists preferred the post treatment side, where 3 preferred the pretreatment side and 1 had no preference. However the preference on dry hair was not so significant different for the panel of five.

| | Panelist # Preference | | |
| --- | --- | --- | --- |
| | N = total | Pre-treatment | Post-treatment |
| Wet Hair* | 11 | 3 | 7 |
| Dry Hair | 5 | 2 | 3 |

*= 1 panelist had no preference

Thus the post-treatment side shows an improvement in the post-perm malodor issue of wet hair. The post treatment composition of the present invention also improved other hair properties including shine, luster, better color retention and better tensile strength recovery.

The post-perm malodor improvement has been further confirmed and verified by salon studies. This salon evaluation included a panel of 7-10 stylists and was based on a rating system of a scale 0-5. Ratings are described below:

| Rating | Malodor Intensity |
|---|---|
| 0-1 | Powerful |
| 1-2 | Strong |
| 2-3 | Medium/Mild |
| 3-4 | Weak/Slight |
| 5 | No odor |

Example 2

Salon half head evaluation has been carried out on four models with Normal hair. The one-half head side was pre-treated with Table 4 composition, and the full head was processed for 20 minutes with wave lotion (N/R) of Table 5. The hair was rinsed, towel blotted and the pre-treated side was neutralized with Neutralizer 1 and the other with Neutralizer 2 of Table 6 containing the fragrance of the present invention. The hair was rinsed and towel blot and the post-treatment composition of the present invention of Table 7 was applied on the side without the pre-treatment.

The tabulated rating odor evaluation result of Table 8 below depicts an improvement in the wet post perm malodor on four models.

TABLE 8

| | Salon Post-Perm Malodor Evaulation - Normal Hair | | | |
|---|---|---|---|---|
| | Initial | | One Week | |
| Mode | Pre-treatment | Post treatment | Pre-treatment | Post treatment |
| 1 | 3 | 4 | 3 | 4 |
| 2 | 3 | 4 | 3 | 4 |
| 3 | 3 | 4 | 2 | 5 |
| 4 | 4 | 5 | 3 | 4 |

Example 3

Salon half-head evaluation of color treated hair has been similarly carried out and processed with the waving lotion (color treated hair) of Table 5. The salon evaluation shows even more pronounced differences between the pre-treatment and post-treatment half-head sides in Table 9 below.

TABLE 9

| | Salon Post-Perm Malodor Evaluation - Color Treated Hair | | | |
|---|---|---|---|---|
| | Initial | | One Week | |
| Model | Pre-treatment | Post-treatment | Pre-treatment | Post-treatment |
| 1 | 2 | 4 | 2 | 4 |
| 2 | 3 | 5 | 3 | 5 |
| 3 | 2 | 4 | 2 | 5 |
| 4 | 2 | 4 | 3 | 4 |
| 5 | 3 | 4 | 3 | 5 |
| 6 | 1 | 3 | 2 | 5 |

The improvement in the post perm mal-odor has also been consistent even after one week of the perm service.

Example 4

The effect of the post-treatment composition on the tensile strength recovery of the fibers has also been demonstrated in Table 11 on normal and color treated hair. The normal and color treated fibers were permed as per Examples 2 and 3 directions without pre-treatment and treated with the post-treatment composition 1, 2 and 3 of the present invention detailed in Table 10.

TABLE 10

| Post-Treatment Composition | | | |
|---|---|---|---|
| Ingredient | % w/w | % w/w | % w/w |
| Hydrolyzed Vegetable Protein PG- Propyl Silanetriol | 0.50 | 2.50 | 5.0 |
| Dimethicone | 0.45 | 0.45 | 0.45 |
| Acetamidopropyl Trimmonium Chloride | 0.37 | 0.37 | 0.37 |
| Fragrance Table 3 | 0.20 | 0.20 | 0.20 |
| Polyquaternium-7 | 0.13 | 0.13 | 0.13 |
| Laureth-23 | 0.11 | 0.11 | 0.11 |
| C11-15 Pareth-9 | 0.075 | 0.075 | 0.075 |
| Tallow Trimmonium chloride | 0.075 | 0.075 | 0.075 |
| Pentasodium Pentetate | 0.05 | 0.05 | 0.05 |
| Methylchloroisothiazolinone | 0.006 | 0.006 | 0.006 |
| Methylisothiazolinone | 0.001 | 0.001 | 0.001 |
| Citric acid QS to pH 3.15 | | | |
| Deionized Water QS to | 100 | 100 | 100 |

The tensile strength recovery as 20% Index for both Normal and Color treated Hair fibers permed fibers is much higher than fibers without the post treatment as shown in Table 11.

TABLE 11

| | 20% Index | | |
|---|---|---|---|
| Study | Post-Treatment | Normal Hair | Colored Treated |
| A | No | 0.830 | 0.829 |
| A | 1 | 0.840 | 0.844 |
| B | No | 0.783 | 0.760 |
| B | 2 | 0.789 | 0.829 |
| C | No | | 0.735 |
| C | 3 | | 0.928 |

It will thus be seen that the objects set forth above, among those made apparent from the proceeding description, are efficiently attained and, since certain changes may be made in carrying out the above method and in the composition set forth without departing from the scope of the invention, it intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

Having described our invention, what we claim as now and desire to secure by Letters Patent is:

The invention claimed is:

1. An odor-reducing post treatment composition for application to permanently waved hair immediately after the completion of the use and removal of a neutralizer, said odor-reducing composition consisting essentially of:
   A. between 0.1% and 2.0% by weight based upon the weight of the entire composition of a hair fixative agent comprising polyquaternium-7;

B. between 0.5% and 3.0% by weight based upon the weight of the entire composition of a conditioning agent comprising dimethicone and tallow trimonium chloride;

C. between 0.1% and 5.0% by weight based upon the weight of the entire composition of a hair strengthening complex comprising hydrolyzed vegetable protein PG-propyl silaneriol;

D. between 0.1% and 0.3% by weight based upon the weight of the entire composition of a fragrance blend, wherein the fragrance blend comprises 4 methyl-4-(methylthio)-2-pentanone, at least one component having a log P ranging between about 1 and 3, and at least two components having a log P greater than 4.0;

E. between 0.01% and 0.3% by weight based on the weight of the entire composition of a chelating agent;

F. between 0.25% and 1.0% by weight based upon the weight of the entire composition of an anti-static agent;

G. between 0.05% and 0.6% by weight based upon the weight of the entire composition of a preservative;

H. between 0.1% and 0.3% by weight based upon the weight of the entire composition of a solubilizer; and I. water forming the balance.

2. The odor-reducing post treatment composition defined in claim 1, wherein the pH of the composition is adjusted to between about 2.5 and 4.0.

3. The odor-reducing post treatment composition defined in claim 1, wherein the fragrance blend further comprises dipropylene glycol and benzyl benzoate as solvents.

4. An odor-reducing post treatment composition for application to permanently waved hair immediately after the completion of the use and removal of a neutralizer, said odor-reducing composition comprising:

A. between 0.01% and 0.30% by weight based upon the weight of the entire composition of pentasodium pentetate;

B. between 0.25% and 1.00% by weight based upon the weight of the entire composition of acetamidopropyl trimonium chloride;

C. between 0.1% and 2.00% by weight based upon the weight of the entire composition of polyquarternium-7;

D. between 0.1% and 0.30% by weight based upon the weight of the entire composition of a solubilizer;

E. between 0.1% and 0.3% by weight based upon the weight of the entire composition of a fragrance blend, wherein the fragrance blend comprises 4-methyl-4-(methylthio)-2-pentanone, at least one component having a log P ranging between about 1 and 3, and at least two components having a log P greater than 4.0;

F. between 0.5% and 2.5% by weight based upon the weight of the entire composition of dimethicone and tallow trimonium chloride;

G. between 0.05% and 0.600% by weight based upon the weight of the entire composition of a preservative;

H. between 0.1% and 5.00% by weight based upon the weight of the entire composition of hydrolyzed vegetable protein PG-propyl silanetriol; and I. water forming the balance.

5. The odor-reducing post treatment composition defined in claim 4, wherein said composition is further defined as comprising:

A. about 0.01% of pentasodium pentetate;

B. about 0.5% of acetamidopropyl trimonium chloride;

C. about 1.5% of polyquarternium-7;

D. about 0.2% of a solubilizer;

E. about 0.2% of the fragrance blend;

F. about 1.5% of a dimethicone and tallow trimonium chloride;

G. about 0.1% of a preservative;

H. about 1.0% of hydrolyzed vegetable protein PG-propyl silanetriol; and

I. water forming the balance.

6. The odor-reducing post treatment composition defined in claim 5, wherein the pH of the composition is adjusted to 3.0.

7. The odor-reducing post treatment composition defined in claim 6, wherein the fragrance blend is further defined as comprising a mixture consisting of 1-1-(1,2,3,4,5,6,7,8-Octahydro-2,3,8,8-tetramethyl-2-naphthalenyl)ethanone; hexamethylindanopyran; Oxacyclohexadecene-2-one; Ethylene Brassylate; Oxacycloheptadec-10-ene-2-one; Dodecahydro-3,8,8,11a-tetramethyl 5H-3,5a-epoxynaphth[2,1-c]oxepin; 7-Methanoazuleno [5,6-b]oxirene 2h-2a; 3,3-dimethyl-5-(2,2,3-trimethyl-3-cyclopenten-1-yl)-4-Penten-2-ol; 2,2,6-trimethyl-a-propyl-cyclohexanepropanol; 4-Methyl-4-(methylthio)-2-pentanone; and 2-Isobutyl-3-methoxypyrazine.

8. The odor reducing post treatment composition defined in claim 4, wherein the fragrance blend is further defined as comprising 2-isobutyl-3-methoxypyrazine as the at least one component having a log P ranging between about 1 and 3.

9. The odor reducing post treatment composition defined in claim 4, wherein the fragrance blend is further defined as comprising dipropylene glycol and benzyl benzoate as solvents.

10. An odor reducing post treatment composition for application to permed or waved hair comprising;

a hair strengthening complex comprising a copolymer of hydrolyzed vegetable protein and silicone; and a fragrance blend capable of effectively eliminating or masking the odor produced by tetrahydroquinoxaline, wherein said fragrance blend consists essentially of 1-1-(1,2,3,4,5,6,7,8-Octahydro-2,3,8,8-tetramethyl-2-naphthalenyl)ethanone; hexamethylindanopyran; Oxacyclohexadecene-2-one; Ethylene Brassylate; Oxacycloheptadec-10-ene-2-one; Dodecahydro-3,8,8,11a-tetramethyl 5H-3,5a-epoxynaphth[2,1-c]oxepin; 7-Methanoazuleno [5,6-b]oxirene 2h-2a; 3,3-dimethyl-5-(2,2,3-trimethyl-3-cyclopenten-1-yl)-4-Penten-2-ol; 2,2,6-trimethyl-a-propyl-cyclohexanepropanol; 4-Methyl-4-(methylthio)-2-pentanone; and 2-Isobutyl-3-methoxypyrazine.

11. An odor-reducing post treatment composition for application to permanently waved hair immediately after the completion of the use and removal of a neutralizer, said odor-reducing composition consisting essentially of:

A. between 0.01% and 0.30% by weight based upon the weight of the entire composition of pentasodium pentetate;

B. between 0.25% and 1.00% by weight based upon the weight of the entire composition of acetamidopropyl trimonium chloride:

C. between 0.1% and 2.00% by weight based upon the weight of the entire composition of polyquarternium-7;

D. between 0.1% and 0.30% by weight based upon the weight of the entire composition of a solubilizer;

E between 0.1% and 0.3% by weight based upon the weight of the entire composition of a fragrance blend comprising 1-1-(1,2,3,4,5,6,7,8-Octahydro-2,3,8,8-tetramethyl-2-napthalenyl)ethanone; hexamethylindanopyran; Oxacyclohexadecene-2-one; Ethylene Brassylate; Oxacycloheptadec-10-ene-2-one; Dodecahydro-3,8,8,11a-tetramethyl 5H-3,5a-epoxynaphth[2,1-c]oxepin; 7-Methanoazuleno [5,6-b]oxirene 2h-2a; 3,3-dimethyl-5-(2,2,3-trimethyl-3-cyclopenten-1-yl)-4-Penten-2-ol;

2,2,6-trimethyl-a-propyl-cyclohexanepropanol; 4-Methyl-4-(methylthio)-2-pentanone; and 2-Isobutyl-3-methoxypyrazine;

F. between 0.5% and 2.5% by weight based upon the weight of the entire composition of dimethicone and tallow trimonium chloride;

G. between 0.05% and 0.600% by weight based upon the weight of the entire composition of a preservative;

H. between 0.1% and 5.00% by weight based upon the weight of the entire composition of hydrolyzed vegetable protein PG-propyl silanetriol; and I. water forming the balance.

12. The odor-reducing post treatment composition defined in claim 11, wherein said composition is further defined as comprising:

A. about 0.01% of pentasodium pentetate;
B. about 0.5% of acetamidopropyl trimonium chloride;
C. about 1.5% of polyquaternium-7;
D. about 0.2% of a solubilizer;
E. about 0.2% of the fragrance blend;
F. about 1.5% of a dimethicone and tallow trimonium chloride;
G. about 0.1% of a preservative;
H. about 1.0% of hydrolyzed vegetable protein PG-propyl silanetriol; and
I. water forming the balance.

13. The odor-reducing post treatment composition defined in claim 12, wherein the pH of the composition is adjusted to 3.0.

14. The odor reducing post treatment composition defined in claim 11, wherein the fragrance blend is further defined as comprising dipropylene glycol and benzyl benzoate as solvents.

* * * * *